United States Patent
Chandraratna et al.

(10) Patent No.: US 9,907,768 B2
(45) Date of Patent: Mar. 6, 2018

(54) RECEPTOR SUBTYPE AND FUNCTION SELECTIVE RETINOID AND REXINOID COMPOUNDS IN COMBINATION WITH IMMUNE MODULATORS FOR CANCER IMMUNOTHERAPY

(71) Applicant: IO Therapeutics, Inc., Seattle, WA (US)

(72) Inventors: Roshantha A. Chandraratna, San Juan Capistrano, CA (US); Martin E. Sanders, Seattle, WA (US)

(73) Assignee: IO THERAPEUTICS, INC., Santa Ana, CA (US)

( * ) Notice: Subject to any disclaimer, the term of this patent is extended or adjusted under 35 U.S.C. 154(b) by 0 days.

(21) Appl. No.: 15/620,411

(22) Filed: Jun. 12, 2017

(65) Prior Publication Data

US 2017/0354623 A1     Dec. 14, 2017

Related U.S. Application Data

(60) Provisional application No. 62/348,646, filed on Jun. 10, 2016, provisional application No. 62/406,779, filed on Oct. 11, 2016.

(51) Int. Cl.
| | |
|---|---|
| *A61K 39/395* | (2006.01) |
| *A61K 31/196* | (2006.01) |
| *A61K 45/06* | (2006.01) |
| *C07K 16/28* | (2006.01) |
| *A61K 39/00* | (2006.01) |

(52) U.S. Cl.
CPC ........ *A61K 31/196* (2013.01); *A61K 39/3955* (2013.01); *A61K 45/06* (2013.01); *C07K 16/2818* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,326,055 A | 4/1982 | Loeliger | |
| 5,234,926 A | 8/1993 | Chandraratna | |
| 5,324,840 A | 6/1994 | Chandraratna | |
| 5,612,356 A | 3/1997 | Yoshimura et al. | |
| 5,723,666 A | 3/1998 | Vuligonda et al. | |
| 5,739,338 A | 4/1998 | Beard et al. | |
| 5,776,699 A | 7/1998 | Klein et al. | |
| 5,824,685 A | 10/1998 | Campochiaro et al. | |
| 5,877,207 A | 3/1999 | Klein et al. | |
| 5,919,970 A | 7/1999 | Song et al. | |
| 5,958,954 A | 9/1999 | Klein et al. | |
| 6,037,488 A | 3/2000 | Song et al. | |
| 6,225,494 B1 | 5/2001 | Song et al. | |
| 6,452,032 B1 | 9/2002 | Beard et al. | |
| 6,455,701 B1 | 9/2002 | Song et al. | |
| 6,653,322 B1 | 11/2003 | Chambon et al. | |
| 2001/0018456 A1 | 8/2001 | Fesus et al. | |
| 2008/0300312 A1 | 12/2008 | Chandraratna | |
| 2009/0176862 A1 | 7/2009 | Chandraratna et al. | |
| 2011/0150892 A1 | 6/2011 | Thudium et al. | |
| 2016/0067336 A1 | 3/2016 | Fandi et al. | |
| 2016/0075783 A1 | 3/2016 | King et al. | |

FOREIGN PATENT DOCUMENTS

| | | |
|---|---|---|
| WO | 200228810 A2 | 4/2002 |
| WO | 2015092420 A1 | 6/2015 |

OTHER PUBLICATIONS

Johnson AT et al. "Synthesis and characterization of a highly potent and effective antagonist of retinoic acid receptors." J Med Chem 38:4764-4767, (1999).
Naidoo J et al. "Immune modulation for cancer therapy" Br. J. Cancer 111:2214-2219, 2014.
Hodi FS et al. "Improved survival with ipilimumab in patients with metastatic melanoma" NEJM 363:711-723, 2010.
Keir ME et al. "PD-1 and its ligands in tolerance and immunity" Ann Rev Immunol 26:677-704, 2008.
Topolian SL et al. "Safety, activity, and immune correlates of anti-PD-1 antibody in cancer" NEJM 366:2443-3454, 2012.
Holmgaard KB et al. :Indoleamine 2,3-dioxygenase is a critical resistance mechanism in antitumor T cell immunotherapy targeting CTLA-4 J Exp Med 210:1389-1402, 2013.
Munn DH et al. "Indoleamine 2,3-dioxygenase and tumor-induced tolerance" J Clin Invest 117:1147-1154, 2007.
Mucida D et al. Reciprocal TH17 and regulatory T cell differentiation mediated by retinoic acid Science 317:256-260, 2007.
Pino-Lagos K et al. "A retinoic acid-dependent checkpoint in the development of CD4+ T cell-mediated immunity" J Exp Med 208:1767-1775, 2011.
Nowak EC et al. "Treatment with retinoid X receptor agonist IRX4204 ameliorates experimental autoimmune encephalomyelitis" Am J Translational Res 8:1016-1026, 2016.
Curiel TJ et al. "Specific recruitment of regulatory T cells in ovarian carcinoma fosters immune privilege and predicts reduced survival." Nat Med 10:942-949, 2004.
Teng M et al. "Identification of highly potent retinoic acid receptor alpha-selective antagonists" J Med Chem 40:2445-2451, 1997.
ISR/WO for PCT/US2017/36870, (2017).

*Primary Examiner* — Sheela J. Huff
(74) *Attorney, Agent, or Firm* — K&L Gates LLP; Louis C. Cullman; David Diamond

(57) ABSTRACT

Disclosed herein are methods for treating cancer comprising administering at least one immune checkpoint inhibitor and at least one Retinoic Acid Receptor or Retinoid X Receptor active agent.

24 Claims, 3 Drawing Sheets

RECEPTOR SUBTYPE AND FUNCTION SELECTIVE RETINOID AND REXINOID COMPOUNDS IN COMBINATION WITH IMMUNE MODULATORS FOR CANCER IMMUNOTHERAPY

CROSS REFERENCE TO RELATED APPLICATIONS

This application claims the benefit of U.S. Provisional patent application 62/348,646 filed Jun. 10, 2016 and 62/406,779 filed Oct. 11, 2016, the entire contents of both of which are incorporated by reference herein.

BACKGROUND

The immune surveillance system provides a host with defense against foreign antigens, but also limits activity against self-antigens thereby preventing autoimmune disease. Cell surface immune checkpoint molecules are endogenous regulators of the immune response which limit autoimmunity by enabling co-inhibitory signaling pathways. Immune checkpoint pathways are important in tumor growth by leading to T-cell depletion and allowing tumors to escape from immune surveillance and enabling unchecked tumor growth. Molecules such as monoclonal antibodies (mAbs) can be designed to target immune checkpoints and such molecules can antagonize co-inhibitory immune pathways, restore immune surveillance, and produce an anti-tumor immune response.

Also, the full anti-tumor effects of immunotherapies can be derived only when they are used in combination with other compounds which can overcome resistance that develop to the immunotherapies by modulating immune pathways.

SUMMARY

Disclosed herein are compounds for potentiation of immune checkpoint targeted therapies. Compounds which act on retinoic acid receptors (RAR) and retinoid X receptors (RXR) potentiate the activity of immune checkpoint targeted agents.

Thus, provided herein are methods of treating cancer, the methods comprising administering at least one immune checkpoint inhibitor and at least one retinoid active agent or rexinoid active agent (collectively RAR/RXR active agents). In some embodiments, the retinoid active agent is a Retinoic Acid Receptor (RAR) active agent. In some embodiments, the rexinoid active agent is a Retinoid X Receptor (RXR) active agent. In some embodiments, two RAR/RXR active agents are used; they can be two RAR active agents, two RXR active agents, or a RAR active agent and a RXR active agent. In some embodiments the RAR/RXR active agent acts as an agonist of its receptor while in other embodiments the RAR/RXR active agent acts as an antagonist of its receptor. In some embodiments utilizing multiple RAR/RXR active agents, the multiple RAR/RXR active agents are formulated and administered separately. In some aspects of these embodiments, the RAR/RXR active agents are administered separately, but during the same treatment session. In other aspects of these embodiments, the RAR/RXR active agents are administered in different treatment sessions. In other embodiments, the multiple RAR/RXR active agents are formulated separately, but co-administered (that is, administered during the same treatment session). In still other embodiments, the multiple RAR/RXR active agents are formulated together as a single, common medicament. In many embodiments, the immune checkpoint inhibitor is an antibody or other polypeptide molecule. Most typically such molecules are administered parenterally. In contrast, the RAR/RXR active agents are small molecules that can be administered orally, for example as pills or capsules and the like. Thus the RAR/RXR active agents and the immune checkpoint inhibitors may be administered on independent schedules.

In some embodiments, the immune checkpoint inhibitor interacts with at least one of CTLA-4, PD-1, TIM-3, LAG-3, PD-L1 ligand, B7-H3, B7-H4, BTLA, ICOS, or OX40. In some embodiments, the immune checkpoint inhibitor is an antibody specific for at least one of CTLA-4, PD-1, TIM-3, LAG-3, PD-L1 ligand, B7-H3, B7-H4, BTLA, ICOS, or OX40.

In some embodiments, the retinoid active agent is a RARα antagonist. In some embodiments, the RARα antagonist is a compound of general formula (I):

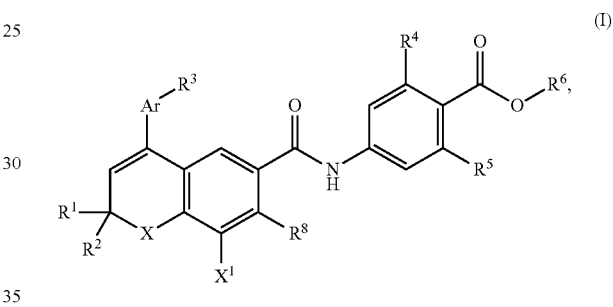

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R^8$ is H or OH.

In some embodiments, the RARα antagonist is AGN194301, AGN193491, AGN193618, AGN194202, or AGN194574.

In some embodiments, the RARα antagonist is a compound of general formula (II):

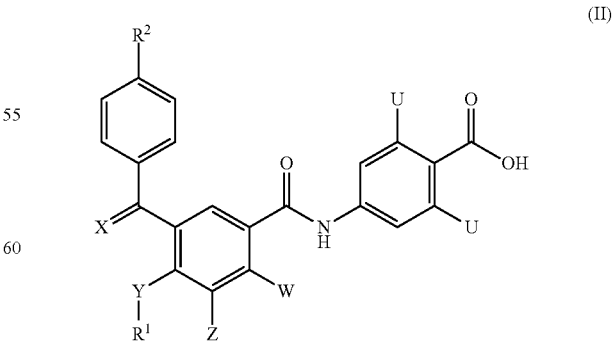

wherein $R^1$ and $R^2$ are independently $C_{1-6}$ alkyl; X is O, S, or $CH_2$; Y is O, S, $CH_2$, or $NR^3$, wherein $R^3$ is $C_{1-6}$ alkyl; Z is Cl or Br; W is H or OH; and U is independently H or F.
In some embodiments, the RARα antagonist is:

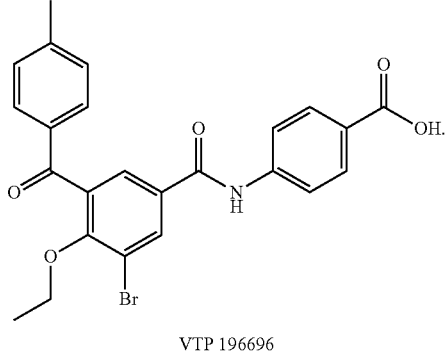 [SMILES: CCOc1c(Br)cc(C(=O)Nc2ccc(C(=O)O)cc2)cc1C(=O)c1ccc(C)cc1]

VTP 196696

In some embodiments, the RARα antagonist is a compound of general formula (III):

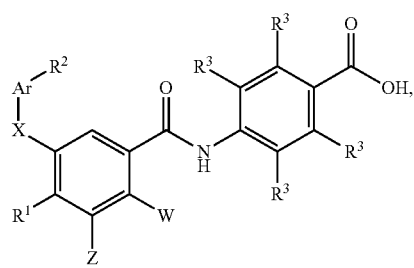

(III)

wherein $R^1$ and $R^2$ are independently H or $C_{1-6}$ alkyl; $R^3$ is H or F; Ar is phenyl, pyridyl, thienyl, furyl, or naphthyl; X is O, S, N, or $CH_2$; W is H or OH; and Z is Cl or Br.

In some embodiments, the RARα antagonist is:

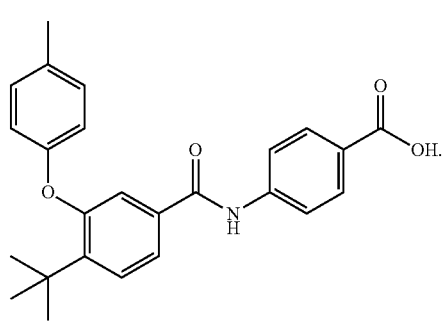

AGN 194777

In some embodiments, the RARα antagonist is BMS185411, BMS614, Ro41-5253, or Ro46-5471.

In some embodiments, the retinoid active agent is a RAR agonist. In some embodiments, the RAR agonist is:

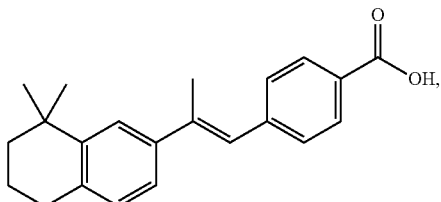

AGN 190183

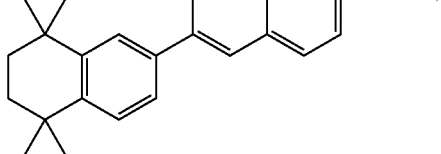

AGN 190205

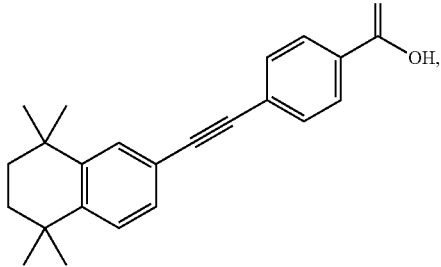

AGN 204647

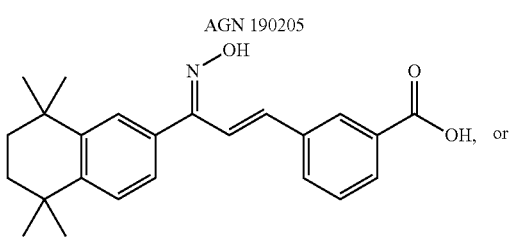

AGN 190168 (Tazarotene)

In some embodiments, the RAR agonist is a RARγ selective agonist of general formula (IV):

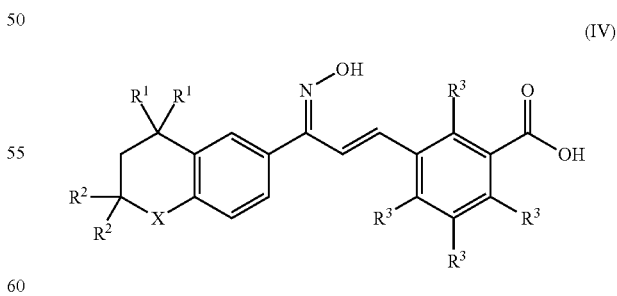

(IV)

wherein $R^1$ and $R^2$ are independently H or $C_{1-6}$ alkyl; $R^3$ is H or F; and X is O, S, $CH_2$, $C(R^4)_2$, or $NR^5$, wherein $R^4$ and $R^5$ are independently H or $C_{1-6}$ alkyl.

In some embodiments, the RAR agonist is a RARγ selective agonist selected from CD437, CD2325, CD666, LY2813631, and BMS961.

In some embodiments, the retinoid active agent is a RXR antagonist. In some embodiments, the RXR antagonist is:

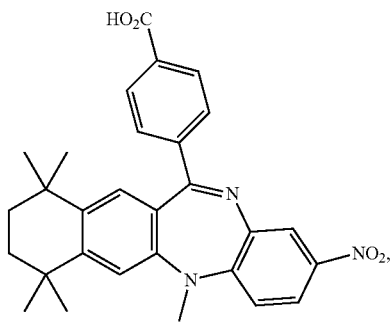

HX 531

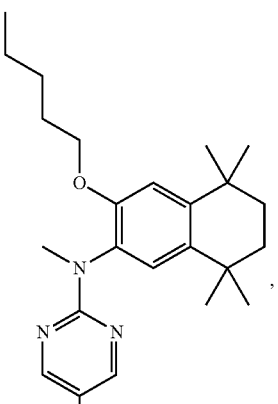

PA 451

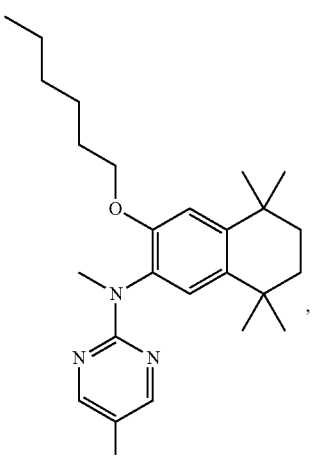

PA 452

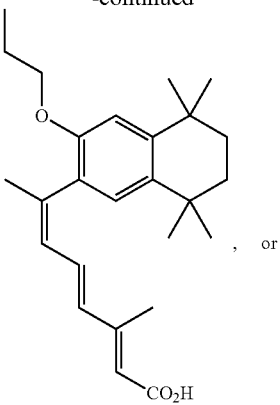

, or

LG 100754

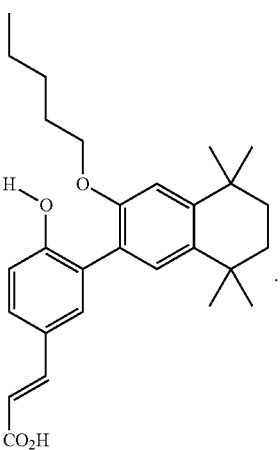

UVI 3003

In some embodiments, the RXR antagonist is AGN195393, or LGN100849.

In some embodiments, the methods comprise additionally administering at least one cancer chemotherapy agent.

In some embodiments, the methods comprise administering at least two retinoid active agents. In some embodiments, the two retinoid active agents are a RARα antagonist and a RARγ agonist.

DETAILED DESCRIPTION

Figure 1A:
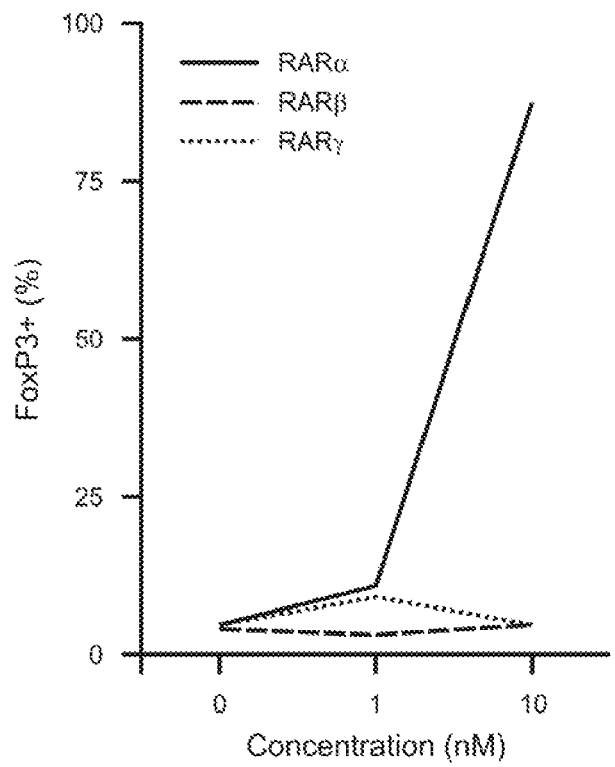
FIG. 1A-C shows that RAR receptor specific agonists regulate FoxP3, α4β7, and CCR9 expression. Purified CD4$^+$ CD25$^-$ FoxP3$^-$ cells were cultured in media with the specified concentration of each RAR agonist and analyzed by flow cytometry for FoxP3 (FIG. 1A), α4β7 (FIG. 1B), and CCR9 (FIG. 10) expression in total CD4 T cells. FoxP3 results are representative of 3 independent experiments. CCR9 and α4β7 results are representative of multiple experiments.

Disclosed herein are compounds for potentiation of immune checkpoint targeted therapies. Compounds which act on retinoic acid receptors (RAR) and retinoid X receptors (RXR) potentiate the activity of immune checkpoint targeted agents. By potentiation it is meant that the immune checkpoint targeted agent has greater and/or more rapid effect when the RAR/RXR active agent is used with the immune checkpoint targeted agent than when the RAR/RXR active agent is not used with the immune checkpoint targeted agent or, similarly, that a given degree of effect can be obtained with a smaller dosage or concentration of the immune checkpoint targeted agent when the RAR/RXR active agent is also used than would be required if the RAR/RXR active agent were not used.

Retinoic acid (RA), at higher pharmacological concentrations, causes anti-inflammatory effects by increasing levels of suppressive $CD4^+$ regulatory T cells (Treg cells). RA affects this function by enhancing expression of the transcription factor Fox P3 which is the master regulator of Treg cell differentiation. RA also reduces the levels of pro-inflammatory Th17 cells. RA elicits these effects by activating the RARα subtype of retinoic acid receptors. The above functions of RA or RARα selective agonists results in these compounds contributing to resistance of tumors to immunotherapy. The increased levels of suppressor Treg cells impede the anti-tumor activity of the T cells produced by immunotherapy. The complement of T cells attacking the tumor is also reduced by the RARα agonist since it reduces the levels of Th17 cells. Conversely, an antagonist of RARα sensitizes tumors to immunotherapy because the RARα antagonist reduces levels of the suppressive Treg cells and also increase levels of the effector Th17 cells. Thus, in one embodiment disclosed herein, a target cancer is treated with a combination of one or more immune checkpoint targeting agents in combination with an RARα antagonist.

In another aspect of RA function, it has been shown that physiological concentrations of RA are critical for the development of T cell mediated immune responses. RA signaling to T cells is a critical early mediator of $CD4^+$ T cell effector function. Using T cells expressing dominant negative RARα (dnRARα), a modified RARα which abrogates RAR function, or a RAR antagonist, it was shown that RA signaling through RARα is required for T cell mediated functions such as skin graft rejection. Thus, in the context of cancer immunotherapy, use of RARα antagonists, or RARα inverse agonists, in combination with immune checkpoint targeting agents has counteracting effects: it can promote anti-tumor effects by decreasing levels of suppressive Treg cells, but such antagonists can also reduce anti-tumor effects by blocking $CD4^+$ T cell effector function. In this context, the use of RARα antagonists in combination with cancer immunotherapy may be of limited value and may even be detrimental.

In another embodiment disclosed herein, the RA signaling that is critical for the development of a T cell mediated immune response is mediated by RARγ. In the above scenario, the sole use of RARα antagonists in conjunction with cancer immunotherapy will result only in a reduction of suppressor Treg cells and consequently in a limited enhancement of the anti-tumor effects of the immunotherapy. However, that approach does not take advantage of the early effects of RA or other RAR agonists acting through RARγ on promoting $CD4^+$ T cell effector function and the potential substantial enhancement of anti-tumor effects of co-administered cancer immunotherapy. Thus, RAR agonists which act specifically through RARγ will promote $CD4^+$ T cell effector function without increasing Treg cells and such RARγ selective agonists will substantially enhance the anti-tumor effects of cancer immunotherapy. In yet another embodiment, the cancer immunotherapy is used to treat a tumor together with a combination of a RARα antagonist and a RARγ agonist. In this situation, the retinoid compounds will enhance the anti-tumor activity of the immunotherapy by the following mechanisms: the RARγ agonist will facilitate the development of a robust $CD4^+$ T cell mediated immune response released by the immune checkpoint blocking agent; the RARα antagonist will reduce the level of suppressor Treg cells and maintain the level of Th17 cells thereby minimizing modulation of the anti-tumor effects of the immunotherapy.

In another embodiment, RXR antagonists promote the formation of suppressor Treg cells and inhibit the formation of effector Th17 cells. The use of a RXR antagonist (or inverse agonist) in combination with cancer immunotherapy will enhance anti-tumor activity by decreasing formation of suppressor Treg cells and by increasing levels of Th17 effector cells.

In summary, the following classes of compounds will be useful in combination to increase the anti-tumor activity of cancer immunotherapy: RARα antagonists, RARγ agonists, and RXR antagonists. In the methods disclosed herein, one or more immune checkpoint-targeting molecules (for example, anti-CTLA-4 antibodies, anti-PD1/PD-L1 antibodies) are administered in combination with one or more of RAR/RXR active agents (for example, RARα antagonists, RARγ agonists, RXR antagonists), with or without other agents to treat certain cancers. The properties of RARα antagonism and RARγ agonism maybe present together in the same molecule. Thus, the same molecule acting as an antagonist at RARα can reduce Treg cell formation and, simultaneously, acting as an agonist at RARγ further reduce Treg cell formation and promote $CD4^+$ T cell effector function. In the same manner, the properties of RXR antagonism may be separately combined with the properties of RARα antagonism or RARγ agonism in distinct molecules. As used herein, the term "retinoid active agents" encompasses, without limitation, any compound acting on a RAR. Non limiting examples of retinoid active agents are RARα antagonists and RARγ agonists. As used herein, the term "rexinoid active agents" encompasses, without limitation, any compound acting on a RXR. A non limiting example of a rexinoid active agent is a RXR antagonist.

The term "agonist" as used herein shall be understood to mean a compound which binds to a receptor and activates it, producing gene transcription and a subsequent pharmacological response (e.g., contraction, relaxation, secretion, enzyme activation, etc.). As used herein, the term "RARγ agonist" refers to a compound that binds to RARγ with a higher affinity compared to binding with another molecule, such as a different RAR. In exemplary embodiments, a RARγ agonist is selective for RARγ over RARα and/or RARβ. Thus, a RAR selective agonist tends to bind to a particular RAR receptor target with high binding affinity. As used herein, the term "agonist" includes selective agonists.

The term "antagonist" as used herein, refers to a compound that attenuates the effect of an agonist by binding in the same site as an agonist without activating the receptor. An antagonist by itself will not affect the gene transcriptional activity of the unoccupied receptor. Conventionally, a RARα antagonist is a chemical agent that inhibits the activity of an RARα agonist. As used herein, the term "RXR antagonist" refers to compounds that bind to RXR and do not activate it, but instead antagonize transcription produced by a RXR agonist. As used herein, the term "antagonist" includes selective antagonists.

The term "inverse agonist" as used herein shall be understood to mean a compound which produces an effect opposite to that of an agonist, yet acts at the same receptor. An inverse agonist by itself will reduce the basal gene transcriptional activity of the unoccupied receptor.

RARα Antagonists

In certain embodiments, the RARα selective antagonist is a compound represented by the general formula (I):

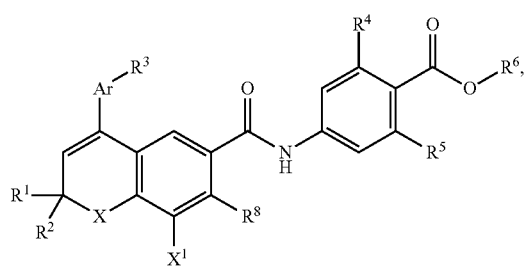

(I)

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R^8$ is H or OH. Each combination of R groups and each combination of their independently selected substituents defines a distinct individual embodiment.

An exemplary RARα selective antagonist of the general formula (I) is the compound AGN194301:

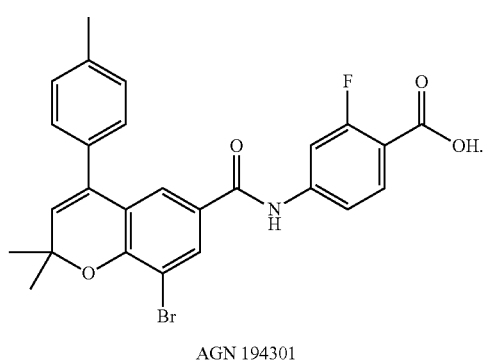

AGN 194301

Other exemplary RARα antagonists of the general class of general formula (I) include, but are not limited to, AGN193491, AGN193618, AGN194202, AGN193625, and AGN194574.

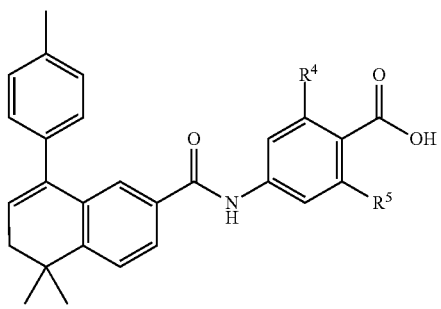

$R^4$ and $R^5$ both H; AGN193491
$R^4$ = F, $R^5$ = H; AGN193618
$R^4$ and $R^5$ both F; AGN194202

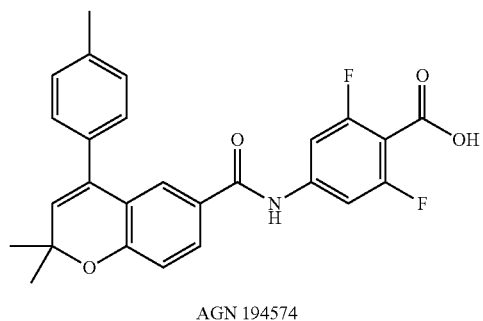

AGN 194574

In other embodiments, the RARα selective agonist is a member of the class of compounds represented by general formula (II)

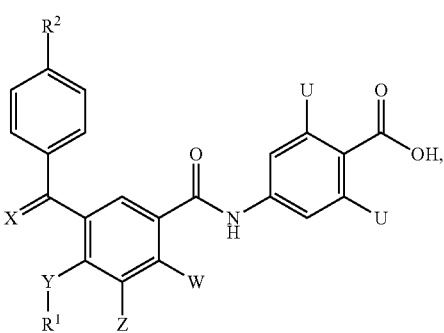

(II)

wherein $R^1$ and $R^2$ are independently $C_{1-6}$ alkyl; X is O, S, or $CH_2$; Y is O, S, $CH_2$, or $NR^3$, wherein $R^3$ is $C_{1-6}$ alkyl; Z is Cl or Br; W is H or OH; and U is independently H or F. Each combination of R groups and each combination of their independently selected substituents defines a distinct individual embodiment.

An exemplary RARα selective antagonist of the class represented by general formula (II) for use in the methods disclosed herein is represented by the following structure (VTP196696):

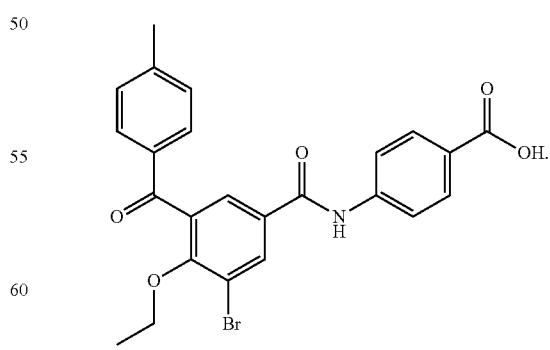

VTP 196696

In other embodiments, RARα selective antagonists are compounds of the general formula (III).

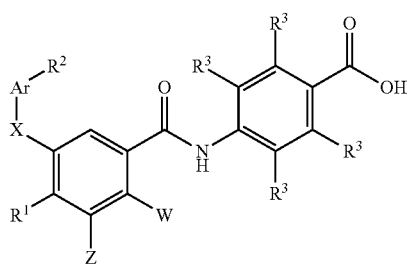

(III)

wherein $R^1$ and $R^2$ are independently H or $C_{1-6}$ alkyl; $R^3$ is H or F; Ar is phenyl, pyridyl, thienyl, furyl, or naphthyl; X is O, S, N, or $CH_2$; W is H or OH; and Z is Cl or Br. Each combination of R groups and each combination of their independently selected substituents defines a distinct individual embodiment.

An exemplary compound of general formula (III) is AGN194777.

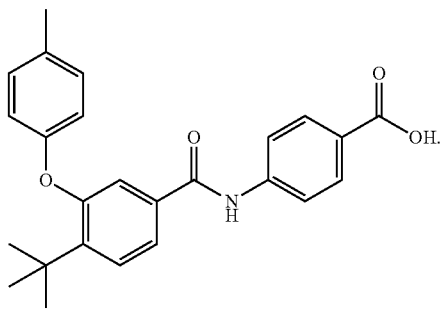

AGN 194777

Other exemplary RARα antagonists include, but are not limited to, BMS185411, BMS614, Ro41-5253, and Ro46-5471.

Additional RAR antagonists or inverse agonists are described in U.S. Pat. Nos. 6,037,488, 5,612,356, 5,776,699, 5,958,954, 5,877,207, 6,225,494, 6,455,701, 5,723,666, 5,739,338, and 5,919,970, and US Patent Application 2009/0176862, all of which are incorporated by reference herein for all they disclose of RAR antagonists.

RARγ Agonists

Exemplary RAR agonists are disclosed in U.S. Pat. Nos. 5,234,926, 4,326,055, 5,324,840, 5,824,685, and 6,452,032, including but not limited to the following compounds.

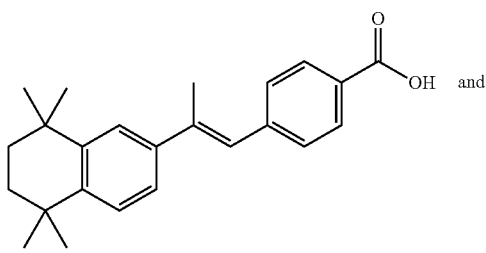

AGN 190183

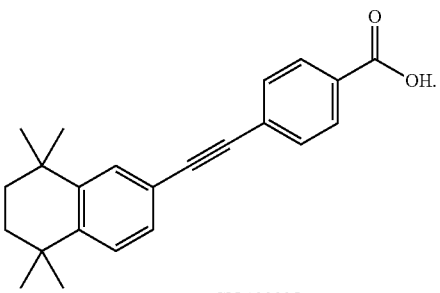

AGN 190205

Another exemplary RAR agonist is AGN 190168.

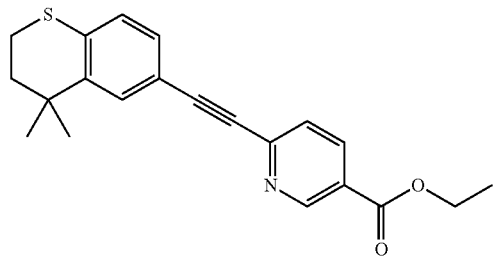

AGN 190168 (Tazarotene)

Although compounds such as AGN190183, AGN190205, AGN190168 (tazarotene) are RARγ agonists they are not RARγ selective since they activate RARα and/or RARβ as well. It may be preferable to use RARγ selective agonists since activation of RARα will inhibit the anti-tumor effects of immune checkpoint targeted agents by negating the T effector cell activation effects produced by RARγ activation by increasing production of Treg cells. RARγ selective agonists, on the other hand, will potentiate the anti-tumor effects of cancer immunotherapeutics.

An example of a highly selective RARγ agonist is the compound AGN204647 (IRX4647):

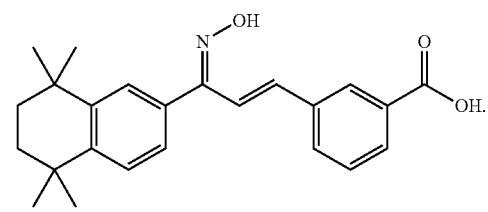

AGN 204647

Other RARγ selective agonists are members of the family of compounds of general formula (IV):

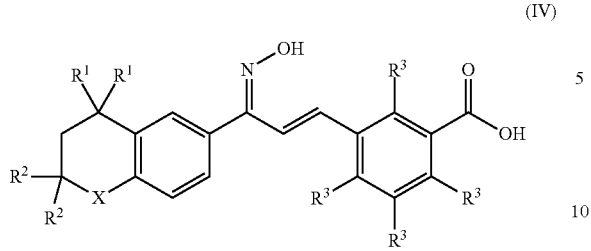

(IV)

wherein $R^1$ and $R^2$ are independently H or $C_{1-6}$ alkyl; $R^3$ is H or F; and X is O, S, $CH_2$, $C(R^4)_2$, or $NR^5$, wherein $R^4$ and $R^5$ are independently H or $C_{1-6}$ alkyl. Each combination of R groups and each combination of their independently selected substituents defines a distinct individual embodiment.

Additional RARγ selective agonists include, but are not limited to, CD437, CD2325, CD666, LY2813631, and BMS961. Additional RARγ agonists are described in International Publication WO 02/28810A2 which is incorporated by reference herein for all it discloses regarding RARγ agonists.

RXR Antagonists

Exemplary RXR antagonists include, but are not limited to, AGN195393, LGN100849, HX531, LG100754, PA451, PA452, and UVI 3003.

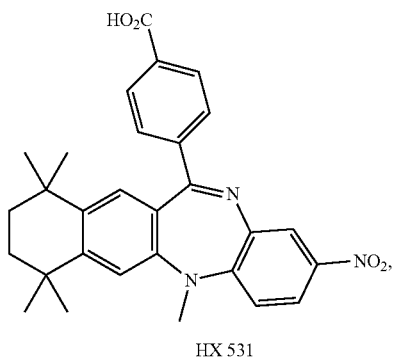

HX 531

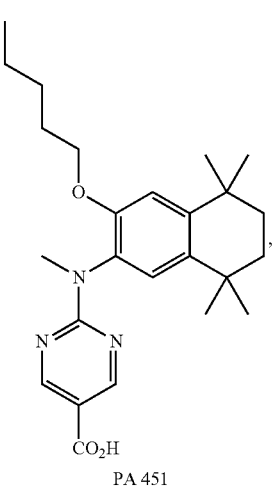

PA 451

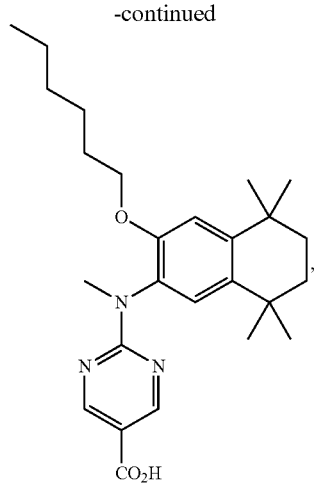

PA 452

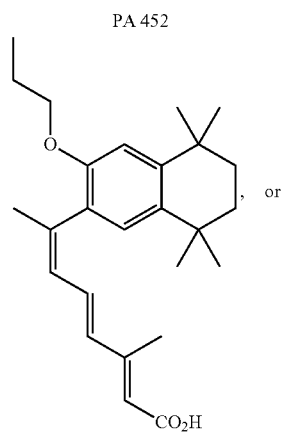

LG 100754

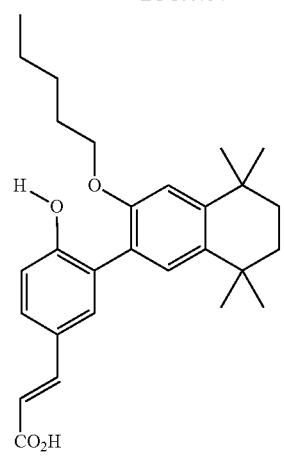

UVI 3003

Immune Checkpoint Targeted Cancer Therapeutics

Immune checkpoint therapy targets regulatory pathways in the differentiation and activation of T cells to promote the passage of T cell developmental program through these checkpoints so that anti-tumor (or other therapeutic) activity can be realized. The agents bringing about immune checkpoint therapy are commonly called immune checkpoint inhibitors and it should be understood that it is the check on T cell development that is being inhibited. Thus, while many immune checkpoint inhibitors also inhibit the interaction of receptor-ligand pairs (e.g., anti-PD-1, anti-PD-L1, and CTLA-4), others (such as anti-OX40 and anti-ICOS) act as agonists of targets that release or otherwise inhibit the check on T cell development, ultimately promoting effector function and/or inhibiting regulatory function.

Disclosed herein is the use of retinoid and rexinoid receptor active molecules (RAR/RXR active agents) as potentiators of the anti-tumor effects of immune checkpoint inhibitor molecules. Molecules which inhibit immune checkpoint proteins include antibodies which are specific to one or more of PD-1, PD-1 ligand, CTLA-4, TIM-3, LAG-3, B7-H3, and B7-H4.

Programmed death-1 (PD-1) is a checkpoint protein on T cells and normally acts as a type of "off switch" that helps keep the T cells from attacking other cells in the body. It does this by binding to programmed death ligand-1 (PD-L1), a protein on some normal and cancer cells. When PD-1 binds to PD-L1, the T cells will not attack the target cells. Some cancer cells have large amounts of PD-L1, which helps them evade immune attack. Monoclonal antibodies that target either PD-1 or PD-L1 can boost the immune response against cancer cells and have shown a great deal of promise in treating certain cancers. Examples of monoclonal antibodies that target PD-1/PL-L1 include: the anti-PD-1 mAbs nivolumab (OPDIVO®, Bristol-Myers Squibb) and pembrolizumab (KEYTRUDA®, Merck & Co.), BMS-936559 (Bristol-Myers Squibb), pidilizumab (Medivation); and the anti-PD-L1 mAbs durvalumab (MEDI4736, IMFINZI™, Medimmune), atezolizumab (MPDL3280A; TECENTRIQ®, Hoffman-La Roche), avelumab (BAVENCIO®, EMD Serono). These antibodies have, variously, demonstrated utility in treating a variety of cancers including malignant melanoma (MM), renal cell carcinoma (RCC), Merkel cell carcinoma, urothelial carcinoma, and non-small cell lung cancer (NSCLC). Non-antibody inhibitors of PD-1/PD-I1 interaction are also being developed; for example, small engineered proteins based on stefin A (called AFFIMER® molecules). In addition to PD-L1, PD-1 can also bind to PD-L2. In addition to PD-1, PD-L1 can also bind to B7-1 (CD80).

CTLA-4 is an immune checkpoint molecule expressed on the surface of CD4 and CD8 T cells and on CD25+, FOXP3+T regulatory (Treg) cells. CTLA-4 generates inhibitory signals that block T cell responses and enables tumor growth. Anti-CTLA-4 mAbs such as ipilimumab (YERVOY®; Bristol-Myers Squibb) cause shrinkage of tumors in animal models. Ipilimumab improves overall survival in MM patients and is approved for the treatment of MM. Responses have been observed in RCC and NSCLC as well. Other exemplary anti-CTLA-4 anitbodies include tremelimumab (Medimmune).

The CTLA-4-blocking antibody ipilimumab gives durable responses only in a subset of melanoma patients and its effects on overall survival is limited. This has led to the search for resistance mechanisms to CTLA-4 blockade and to the identification of the cytosolic enzyme indoleamine 2,3-dioxygenase (IDO) as a potent mediator of melanoma resistance. IDO directly suppresses effector T cells and activates suppressive Treg cells thereby modulating the anti-tumor effects of CTLA-4 blockade. Inhibitors of IDO such as 1-methyl-tryptophan have T cell dependent anti-tumor effects and synergize with CTLA-4-blocking antibody to control tumor growth and enhance survival.

TIM-3 (T-cell immunoglobulin and mucin-domain containing-3) is a molecule selectively expressed on IFN-γ—producing CD4$^+$ T helper 1 (Th1) and CD8$^+$ T cytotoxic 1 (Tc1) T cells. TIM-3 is an immune checkpoint receptor that functions specifically to limit the duration and magnitude of Th1 and Tc1 T-cell responses. Exemplary antibodies to TIM-3 are disclosed in U.S. Patent Application Publication 20160075783 which is incorporated by reference herein for all it contains regarding anti-TIM-3 antibodies.

LAG-3 (lymphocyte-activation gene 3; CD223) negatively regulates cellular proliferation, activation, and homeostasis of T cells, in a similar fashion to CTLA-4 and PD-1 and plays a role in Treg suppressive function. Exemplary antibodies to LAG-3 include GSK2831781 (GlaxoSmithKline), BMS-986016 (Bristol-Myers Squibb) and the antibodies disclosed in U.S. Patent Application Publication 2011/0150892 which is incorporated by reference herein for all it contains regarding anti-LAG-3 antibodies.

The B7 family is a family of costimulatory proteins which are expressed on the surface of antigen-presenting cells and interact with ligands on T cells. B7-H3 (CD276) is one of the molecules in this family. An antibody to B7-H3, enoblituzumab (EMPLICITI™, Bristol-Myers Squibb) is approved for treatment of multiple myeloma. Another molecule in the family is B7-H4 (V-set domain-containing T-cell activation inhibitor 1), antibodies against which are in development.

Other immune checkpoint inhibitor targets, B- and T-cell attenuator (BTLA), inducible T-cell costimulator (ICOS), OX40 (tumor necrosis factor receptor superfamily, member 4), and others are potentially useful in the disclosed methods. Several anti-OX40 agonistic monoclonal antibodies are in early phase cancer clinical trials including MEDI0562 and MEDI6469 (Medimmune), MOXR0916 (Genetech), and PF-04518600 (Pfizer); as is an anti-ICOS agonistic antibody, JTX-2011 (Jounce Therapeutics).

Disclosed herein are methods of potentiating the anti-cancer activity of immune checkpoint targeting immunotherapeutics including a CTLA-4 inhibitor, a PD-1 inhibitor, a TIM-3 inhibitor, a LAG-3 inhibitor, a PD-1 ligand (such as PDL-1), an inhibitor of a PD-1 ligand, an OX40 agonist, an ICOS agonist, a B7-H3 protein, an inhibitor of a B7-H3 protein, a B7-H4 protein, and an inhibitor of a B7-H4 protein. In certain embodiments, the inhibitors are antibodies.

The immune checkpoint targeting immunotherapeutic antibodies can be whole antibodies or antibody fragments. The terms "fragment of an antibody," "antibody fragment," and "functional fragment of an antibody" are used interchangeably herein to mean one or more fragments of an antibody that retain the ability to specifically bind to an antigen. The antibody fragment desirably comprises, for example, one or more complementary determining regions (CDRs), the variable region (or portions thereof), the constant region (or portions thereof), or combinations thereof. Examples of antibody fragments include, but are not limited to, a Fab fragment, which is a monovalent fragment consisting of the $V_L$, $V_H$, $C_L$, and $CH_1$ domains; a F(ab')$_2$ fragment, which is a bivalent fragment comprising two Fab fragments linked by a disulfide bridge at the hinge region; a Fv fragment consisting of the $V_L$ and $V_H$ domains of a single arm of an antibody; a single chain Fv, in which the $V_L$ and $V_H$ domains are joined by a peptide linker sequence; a Fab' fragment, which results from breaking the disulfide bridge of an F(ab')$_2$ fragment using mild reducing conditions; a disulfide-stabilized Fv fragment (dsFv); and a domain antibody (dAb), which is an antibody single variable region domain (VH or VL) polypeptide that specifically binds antigen.

In alternative embodiments the antibody is replaced with another protein that similarly binds to the immune checkpoint target molecule. In some instances these non-antibody molecules comprise an extracellular portion of the immune checkpoint target molecule's ligand or binding partner, that is, at least the extracellular portion needed to mediate binding to the immune checkpoint target molecule. In some embodiments this extracellular binding portion of the ligand is joined to additional polypeptide in a fusion protein. In some embodiments the additional polypeptide comprises an Fc or constant region of an antibody.

Methods of Treatment

Provided herein are methods of treating cancer in a mammal by administering an antibody (or other polypeptide capable of binding) to an immune checkpoint molecule and one or more RAR/RXR active agents. Other embodiments relate to compositions comprising such agents for use in the treatment of cancer and for use in making medicaments for the treatment of cancer. It is to be understood that the multiple agents used may be provided in separate compositions or medicaments which may be administered by separate routes of administration and/or at separate times; nonetheless use of such multiple compositions or medicaments is coordinated so that the patient to whom they are administered receives the benefit of the combined, interacting activity of the multiple agents.

In some embodiments, the method comprises administering an immune checkpoint inhibitor and an RAR active agent. In some embodiments, the method comprises administering an immune checkpoint inhibitor and an RARα antagonist. In some embodiments, the method comprises administering an immune checkpoint inhibitor and an RARγ agonist. In some embodiments, the method comprises administering an immune checkpoint inhibitor and two RAR active agents. In some embodiments, the method comprises administering an immune checkpoint inhibitor and an RARα antagonist an RAR agonist. In some embodiments, the method comprises administering an immune checkpoint inhibitor and an RARα antagonist an RARγ selective agonist. In certain embodiments, the RARα antagonist is AGN194301, AGN193491, AGN193618, AGN194202, AGN194574, VTP196696, AGN19477, BMS185411, BMS614, Ro41-5253, or Ro46-5471. In some embodiments the RAR agonist is AGN190183, AGN190205, AFN204647, or tazarotene. In some embodiments, the RARγ selective agonist is CD437, CD2325, CD666, LY2813631, or BMS961.

In some embodiments, the method comprises administering an immune checkpoint inhibitor and an RXR active agent. In some embodiments, the method comprises administering an immune checkpoint inhibitor and an RXR antagonist. In some embodiments, the RXR antagonist is AGN195393 or LGN100849. With respect to the use of multiple RAR/RXR active agents in the various use or method of treatment embodiments described herein, any of the disclosed general formula genera, sub-genera thereof, and individual species may be combined with any other general formula genera, sub-genera thereof, and individual species, each such combination defining an individual embodiment.

The disclosed methods can be used to treat any type of cancer known in the art, such as, for example, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In select embodiments a particular type of cancer is treated. In other select embodiments a particular type of cancer is excluded from treatment.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the immune checkpoint inhibitor and one or more retinoid or rexinoid active agents to elicit a desired response in the individual. For example, a therapeutically effective amount of a retinoid-active agent of the invention is an amount which increases the anti-cancer activity of an immune checkpoint inhibitor antibody or polypeptide.

The term "treating" or "treatment" broadly includes any kind of treatment activity, including the diagnosis, mitigation, or prevention of disease in man or other animals, or any activity that otherwise affects the structure or any function of the body of man or other animals. Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used— by a policy or practice standard as might be established by a hospital, clinic, health maintenance organization, medical practice or physicians group, and the like.

A typical dose of an immune checkpoint inhibitor antibody or polypeptide can be, for example, in the range of 1 pg/kg to 20 mg/kg of animal or human body weight; however, doses below or above this exemplary range are within the scope of the present disclosure. The daily dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µkg, about 1 mg/kg, about 5 mg/kg, about 10 mg/kg, or a range defined by any two of the foregoing values), from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease or disease symptoms occurs. However, other dosage regimens may be useful and are within the scope of the invention. The desired dosage can be delivered by a single bolus administration of the composition, by multiple bolus administrations of the composition, or by continuous infusion administration of the composition.

Typical doses of RARα antagonists are 0.01 to 300 mg/m$^2$/day; however, doses below or above this exemplary range are within the scope of the present disclosure. The daily dose can be about 0.5 to 100 mg/m$^2$/day, 1 to 90 mg/m$^2$/day, 5 to 80 mg/m$^2$/day; or at least 0.02, 0.03, 0.05, 0.07, 0.1, 0.2, 0.3, 0.5, 0.7, 1, 2, 3, 5, 7, 10, 15, 20, 25, 30, 50, 70 or 100 mg/m$^2$/day; or not more than 0.1, 0.2, 0.3, 0.5, 0.7, 1, 2, 3, 5, 7, 10, 15, 20, 25, 30, 50, 60, 70. 80, 90, 100, 125, 150, 175, 200, 225, 250, 275, or 300 mg/m$^2$/day; or a range defined by any two of the foregoing values.

Typical doses of RARγ agonists are 0.01 to 300 mg/m$^2$/day; however, doses below or above this exemplary range are within the scope of the present disclosure. The daily dose can be about 0.5 to 100 mg/m$^2$/day, 1 to 90 mg/m$^2$/day, 5 to 80 mg/m$^2$/day; or at least 0.02, 0.03, 0.05, 0.07, 0.1, 0.2, 0.3, 0.5, 0.7, 1, 2, 3, 5, 7, 10, 15, 20, 25, 30, 50, 70 or 100 mg/m$^2$/day; or not more than 0.1, 0.2, 0.3, 0.5, 0.7, 1, 2, 3, 5, 7, 10, 15, 20, 25, 30, 50, 60, 70. 80, 90, 100, 125, 150, 175, 200, 225, 250, 275, or 300 mg/m$^2$/day; or a range defined by any two of the foregoing values.

Typical doses of RXR antagonists are 0.01 to 300 mg/m$^2$/day; however, doses below or above this exemplary range are within the scope of the present disclosure. The daily dose can be about 0.5 to 100 mg/m$^2$/day, 1 to 90 mg/m$^2$/day, 5 to 80 mg/m$^2$/day; or at least 0.02, 0.03, 0.05, 0.07, 0.1, 0.2, 0.3, 0.5, 0.7, 1, 2, 3, 5, 7, 10, 15, 20, 25, 30, 50, 70 or 100 mg/m$^2$/day; or not more than 0.1, 0.2, 0.3, 0.5, 0.7, 1, 2, 3, 5, 7, 10, 15, 20, 25, 30, 50, 60, 70. 80, 90, 100, 125, 150, 175, 200, 225, 250, 275, or 300 mg/m$^2$/day; or a range defined by any two of the foregoing values.

The average surface area of a human body is generally accepted to be 1.9 m$^2$ for an adult male, 1.6 m$^2$ for an adult female, and 1.33 m$^2$ for a 12-13 year old child. These values can be used to calculate dose ranges for daily dosage for the values in the preceding paragraphs. The total daily dosage of RAR/RXR active agents can be administered as a single dose or as two doses administered with a 24 hour period spaced 8 to 16, or 10 to 14, hours apart. The RAR/RXR active agents are administered in coordination with the immune checkpoint inhibitor(s) and as above therapeutic or prophylactic efficacy can be monitored by periodic assessment of treated patients. For repeated administrations over several days or longer, depending on the condition, the treatment can be repeated until a desired suppression of disease or disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The immune checkpoint inhibitor antibodies and retinoid or rexinoid active agent can be administered to a mammal using standard administration techniques, including oral, intravenous, intraperitoneal, subcutaneous, pulmonary, transdermal, intramuscular, intranasal, buccal, sublingual, or suppository administration. The checkpoint inhibitor composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection. The retinoid or rexinoid active agent preferably is suitable for oral administration, for example as a pill, tablet or capsule.

The immune checkpoint inhibitor antibodies and retinoid or rexinoid active agents disclosed herein of the invention may be administered at substantially the same time (within 1 hr of each other) or at different times. In some embodiments, the subject is pre-treated with a retinoid or rexinoid active agent at least 30 min, at least 1 hr, or at least 2 hr before administration of the immune checkpoint inhibitor antibody or polypeptide. In some embodiments, the retinoid or rexinoid active agent is administered after the onset of immune checkpoint inhibitor antibody or polypeptide administration.

The immune checkpoint inhibitor antibodies and retinoid or rexinoid active agents disclosed herein may be administered in combination with other drugs, such as at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery. In other embodiments the immune checkpoint inhibitor antibodies and retinoid or rexinoid active agents are the only therapeutic reagents administered or the only treatment given; or the only treatment or reagents given, the primary utility of which is to promote an anti-cancer immune response; or the only treatment or reagents given, the primary utility of which is to promote a T cell-mediated anti-cancer immune response.

EXAMPLES

The following non-limiting examples are provided for illustrative purposes only in order to facilitate a more complete understanding of representative embodiments now contemplated. These examples should not be construed to limit any of the embodiments described in the present specification.

Example 1

RARα Signaling Induces Foxp3 Expression

Figure 1B:
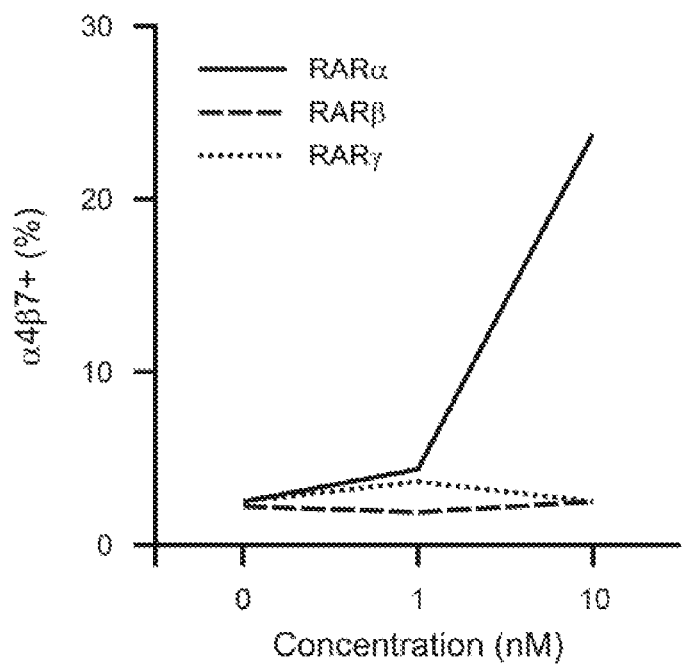
Figure 1C:
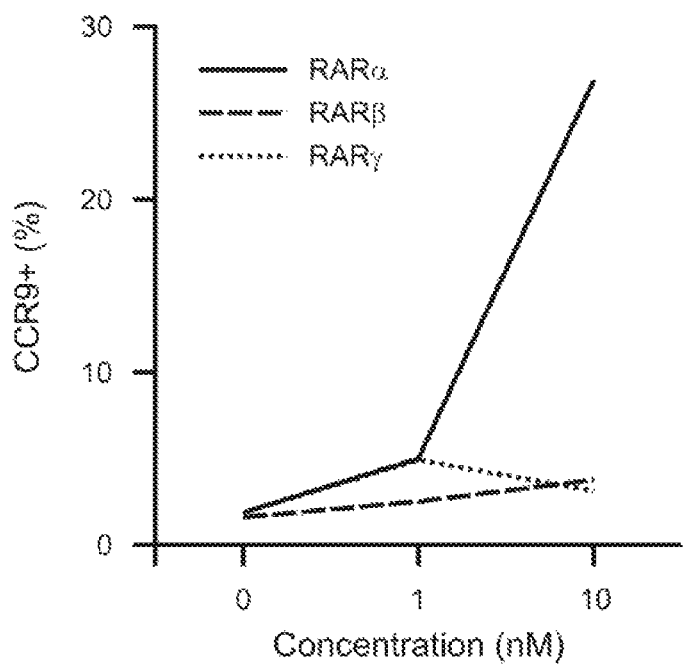

It is important to determine which of the RAR (RARα, RARβ, RARγ) signaling pathways is important in the induction of Foxp3 expression. To determine this, naive CD4$^+$ CD25$^-$ FoxP3$^-$ cells were purified from a Foxp3-GFP mouse using flow cytometry by sorting and isolating based upon a GFP$^-$ phenotype. These cells were activated polyclonally with αCD3 in vitro in the presence of IL-2 and TGF-β. To identify the RAR involved in RA-induced Foxp3 expression, the cultured cells were incubated with RAR selective agonists. The cultured cells were then scored for the frequency of GFP$^+$ (Foxp3$^+$). With respect to the use of selective agonists, only the RARα agonist exerted significant impact on the expression of Foxp3 inducing nearly 100% Foxp3+ T cells, with enhancement on the expression of α4β7 and CCR9 (gut homing receptors) (FIG. 1). The RARγ and RARβ agonists were without effect. These results indicate that RARα selective agonists could be useful in reducing a symptom of inflammation or an autoimmune disorder. Conversely, RARα selective antagonists or inverse agonists could be useful to downregulate the production of immunosuppressive Treg cells thereby promoting an immune response, such as an anti-cancer immune response.

Example 2

Compound 5183 is RARα Specific

Figure 2:
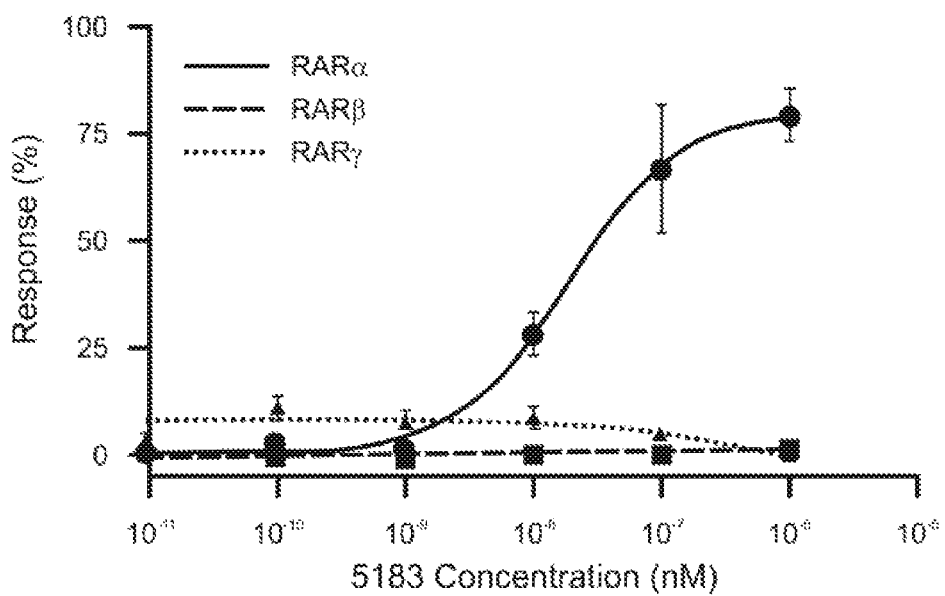
FIG. 2 shows the extent that compound 5183 activates transcription from RARα, RARβ, and RARγ using a trans-activation assay.
Figure 3A:
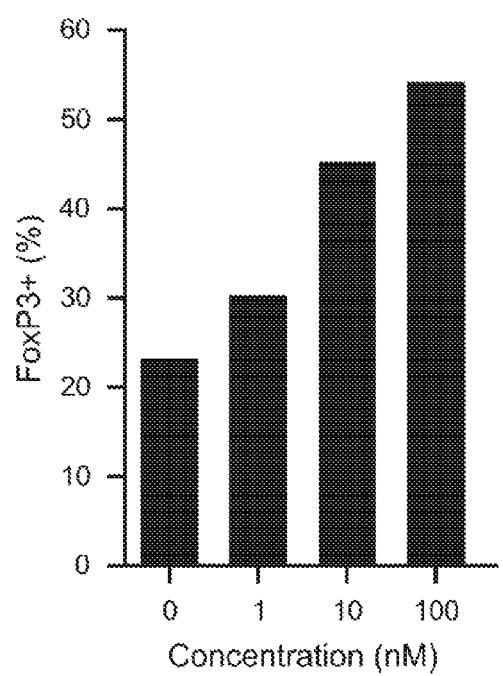
FIG. 3 A-B shows the extent to which the RXR specific agonist, IRX4204 promotes the formation of FoxP3+ Treg cells and inhibits the formation of Th 17 cells.
Figure 3B:
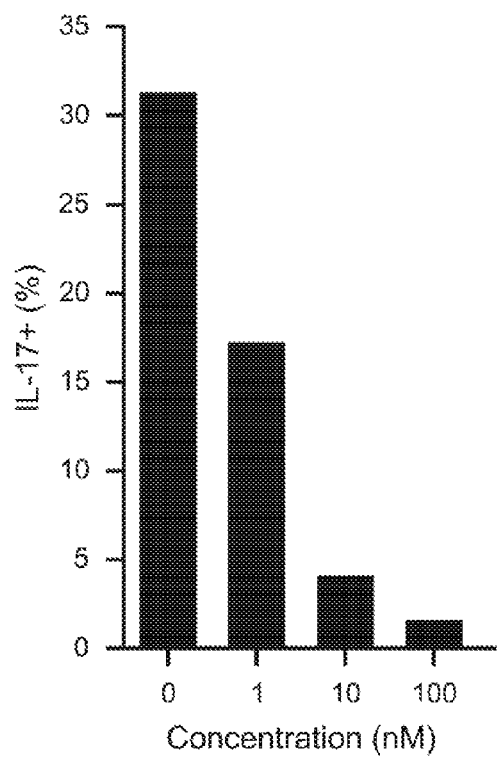

To determine whether the compounds having a structure of formula I are RARα selective agonists, the compound 5183 was examined for its ability to bind to RARα, RARβ, and RARγ using a displacement assay to measure agonist binding affinity and a transactivation assay to measure agonist activity. These results indicate that compound 5183 selectively binds to RARα with high affinity (Table 1) and specifically activates RARα (FIG. 2). Such a RARα selective agonist could minimize the adverse effects related to pan-activation including mucocutaneous toxicity, headache, and proinflammatory events in clinical studies.

TABLE 1

5183 Binding Affinities for RARα, RARβ, and RARγ

| RARα | RARβ | RARγ |
| --- | --- | --- |
| 4.7 nM | >10,000 nM | >10,000 nM |

Example 3

RARα Selective Agonists Regulates T Cell Differentiation

To determine whether a RARα selective agonist could affect T cell differentiation, T cells were incubated with a RARα selective agonist to determine its effect on Foxp3 expression. Naive $CD4^+$ $CD25^-$ $FoxP3^-$ cells were purified from a Foxp3-GFP mouse using flow cytometry by sorting and isolating based upon a $GFP^-$ phenotype. These cells were activated polyclonally with αCD3 in vitro in the presence of IL-2 and TGF-β. These cells were then cultured in media with various concentrations of compound 5183 (a RARα selective agonist) and the expression of FoxP3-GFP was analyzed by flow cytometry. The RARα selective agonist compound 5183 enhanced differentiation of immunosuppressive Treg cells and inhibited differentiation of inflammatory TH17 cells from naïve T cells in vitro (Table 2).

TABLE 2

RARα agonist Effects on T Cell Differentiation

| | Treg cell | | Th17 cell | |
| --- | --- | --- | --- | --- |
| RARα agonist | Concentration (nM) | Percent Differentiation (%) | Concentration (nM) | Percent Differentiation (%) |
| Compound 5183 | 0 | 25 | 0 | 32 |
| | 0.1 | 26 | 0.1 | 32 |
| | 1 | 55 | 1 | 21 |
| | 10 | 90 | 10 | 11 |
| | 100 | ND | 100 | 5 |

To expand on the finding above, the in vivo effects of a RARα selective agonist on T cell differentiation was evaluated in a mouse model. Mice were treated with 100 μg of compound 5183 (a RARα agonist) or an equivalent volume of DMSO (vehicle control) every other day for 10 days. Lympocytes from the blood and spleen were then isolated and FoxP3 expression in $CD4^+$ T cells was assessed. The data shows that following administration of compound 5183 there was a significant increase in the percentage of Foxp3+ T cells in the spleen and blood of treated mice (Table 3). A two-fold increase in Treg cells should impact significantly on the overall immunity in the host by reducing immune responses.

TABLE 3

RARα agonist Effects on T Cell Differentiation

| | Foxp3+ Expression (%) | |
| --- | --- | --- |
| Tissue | DMSO | Compound 5183 |
| Blood | 2.4 | 4.3 |
| Spleen | 10 | 25 |

Conversely, AGN196996, an RARα selective antagonist, increases Th17 cell numbers and decreases Treg cell numbers in the above in vitro and in vivo assays. Consequently, RARα antagonists increase the immune response and potentiate the anti-tumor effects of immune checkpoint blocking antibodies.

Example 4

Binding of Test Compounds to RAR and RXR Receptors and Activation of Reporter Genes Retinoic acid receptor transactivation activity and binding efficiencies are determined essentially as described in U.S. Pat. Nos. 5,298,429 and 5,071,773, incorporated by reference herein. Transactivation assays employ expression plasmids encoding the full length receptors RARα, RARβ, RARγ, RXRα, RXRβ, and RXRγ. Reporter plasmids containing the herpes virus thymidine kinase promoter and the appropriate retinoic acid receptor response element (RAREs) or retinoid X receptor response element (RXREs) are positioned upstream of an open coding region encoding firefly luciferase.

Binding assays are performed using a classic competition assay format in which cloned receptor RAR and RXR molecules are first loaded with either radiolabeled all-trans-retinoic acid (RAR) or radiolabeled 9-cis retinoic acid (RXR), and then the amount of radioactivity liberated with increasing concentration of test compound is measured.

The assays are used to identify RARα selective antagonists, RARγ selective agonists and RXR selective antagonists as disclosed herein above.

Example 5

Pharmacological Activation of RARγ Signaling Using RARγ Agonists has a Cooperative Effect with Anti-CTLA-4 Antibody in Rejection of B 16 Melanoma Cells The anti-tumor effects of anti-CTLA-4 antibody treatment combined with 10 nM RARγ agonist (AGN204647 (IRX4647)) are examined in C57BL/6 mice engrafted with B16F10 tumor cells. Mice treated with vehicles only do not show a survival advantage (0%) over untreated control mice. The survival rate of the mice treated with anti-CTLA-4 antibody alone is 40% at 50 days while the mice treated with RARγ agonist alone have a 30% survival in the same time. Remarkably, mice treated with both anti-CTLA-4 antibody and RARγ agonist have a 100% survival at 50 days indicating that these two agents cooperate to eliminate the B16 melanoma cells. Surviving mice that undergo combination treatment are resistant to re-challenge with twice the dose of live tumor cells indicating the effective formation of B16-specific memory cells. Importantly, the anti-melanoma effect is obtained with this combination of drugs without signs of acute or delayed toxicity Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating cancer comprising administering at least one immune checkpoint inhibitor, wherein the immune checkpoint inhibitor comprises an antibody specific for at least one of CTLA-4, PD-1, TIM-3, LAG-3, PD-L1, B7-H3, B7-H4, BTLA, ICOS, or OX40, and at least one retinoid active agent wherein the at least one retinoid active agent comprises a first Retinoic Acid Receptor (RAR) active agent that is a RAR agoinst, and wherein the RAR agonist is a RARγ selective agonist of general formula IV

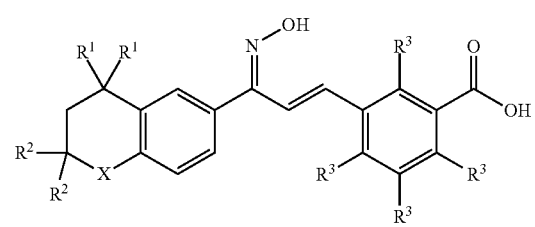

wherein $R^1$ and $R^2$ are independently H or $C_{1-6}$ alky; $R^3$ is H or F; X is O, S, $CH_2$, $C(R^4)_2$, or $NR^5$; and $R^4$ and $R^5$ are independently H or $C_{1-6}$ alkyl.

2. The method of claim 1, further comprising administering a second RAR active agent.

3. The method of claim 2, wherein the second RAR active agent is a RARα selective antagonist that is:

(i) a compound of general formula (I)

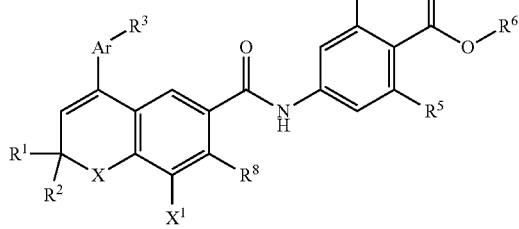

wherein $R^1$, $R^2$, $R^3$, and $R^6$ are independently H or $C_{1-6}$ alkyl; $R^4$ and $R^5$ are independently H or F; Ar is phenyl, pyridyl, thienyl, furyl, or naphthyl; X is $C(CH_3)_2$, O, S, or $NR^7$, wherein $R^7$ is H or $C_{1-6}$ alkyl; $X^1$ is H or halogen such as F, Cl or Br; and $R^8$ is H or OH;

(ii) a compound of general formula (II)

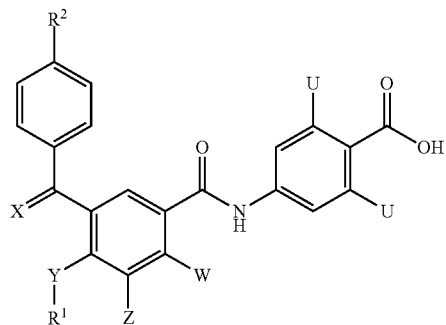

wherein $R^1$ and $R^2$ are independently $C_{1-6}$ alkly; X is O, S, or $CH_2$; Y is O, S, $CH_2$, or $NR^3$, wherein $R^3$ is $C_{1-6}$ alkyl; Z is Cl or Br; W is H or OH; and U is independently H or F;

(iii) a compound of general formula (III)

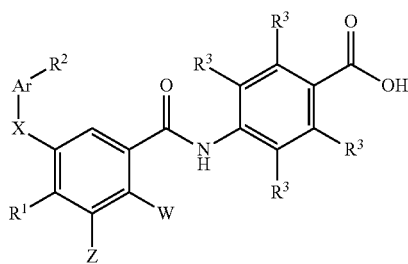

wherein $R^1$ and $R^2$ are independently H or $C_{1-6}$ alkyl; $R^3$ is H or F; Ar is phenyl, pyridyl, thienyl, furyl, or naphthyl; X is O, S, N, or $CH_2$; W is H or OH; and Z is Cl or Br; or

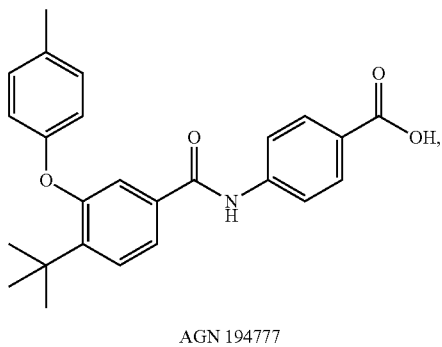 [SMILES: Cc1ccc(Oc2cc(C(=O)Nc3ccc(C(=O)O)cc3)ccc2C(C)(C)C)cc1]

AGN 194777

BMS185411, BMS614, Ro41-5253, or Ro46-5471.

4. The method of claim 3, wherein the RARα antagonist is a compound of general formula (I).

5. The method of claim 4, wherein the RARα antagonist is:

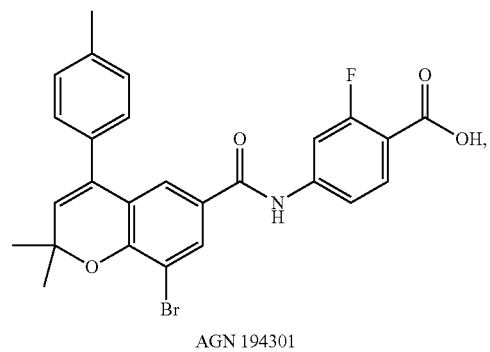

AGN 194301

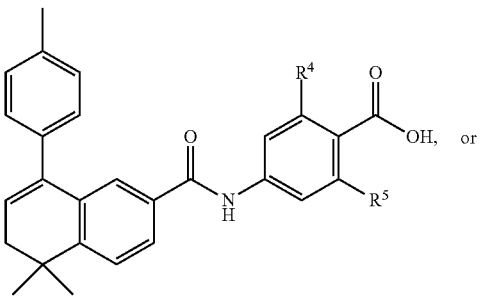

I. $R^4$ and $R^5$ both H; AGN193491
II. $R^4$ = F, $R^5$ = H; AGN193618, or
III. $R^4$ and $R^5$ both F; AGN194202

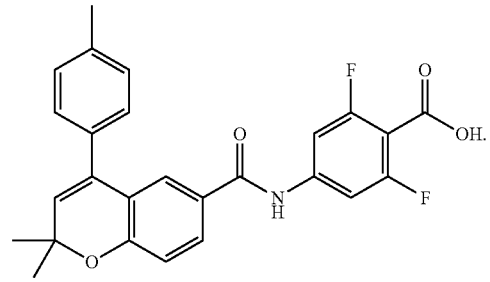

AGN 194574

6. The method of claim 3, wherein the RARα antagonist is a compound of general formula (II).

7. The method of claim 6, wherein the RARα antagonist is:

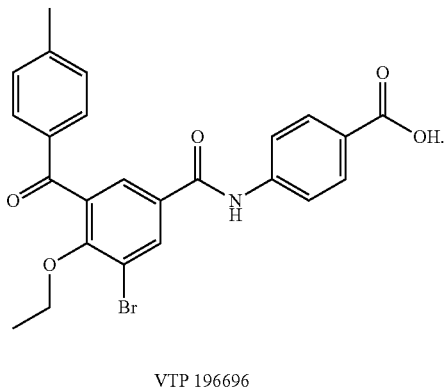 [SMILES: CCOc1c(Br)cc(C(=O)Nc2ccc(C(=O)O)cc2)cc1C(=O)c1ccc(C)cc1]

VTP 196696

8. The method of claim 3, wherein the RARα antagonist is a compound of general formula (III).

9. The method of claim 3, wherein the RARα antagonist is:

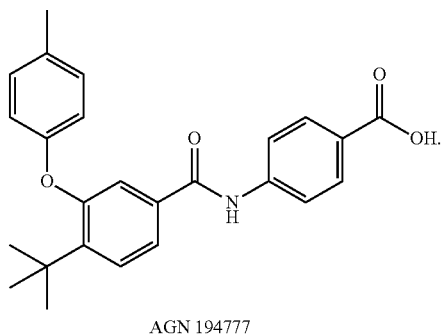 [SMILES: Cc1ccc(Oc2cc(C(=O)Nc3ccc(C(=O)O)cc3)ccc2C(C)(C)C)cc1]

AGN 194777

10. The method of claim 3, wherein the RARα antagonist is BMS185411, BMS614, Ro41-5253, or Ro46-5471.

11. The method of claim 2, wherein the second RAR active agent is an RAR agonist selected from:

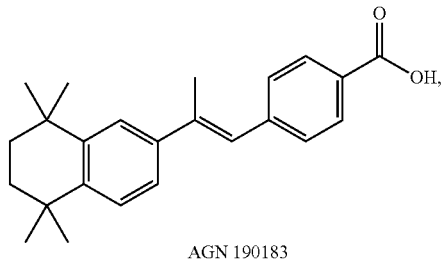

AGN 190183

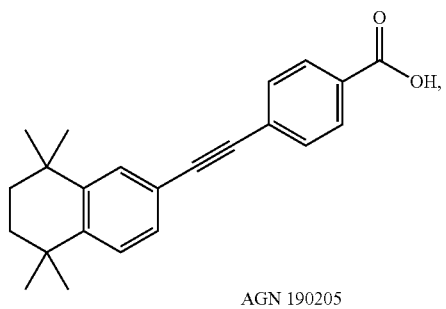

AGN 190205

-continued

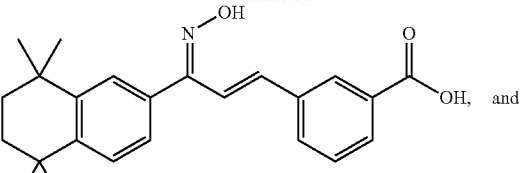

AGN 204647

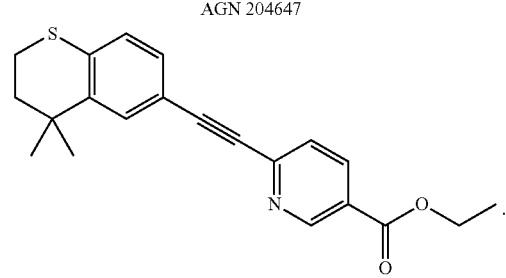

AGN 190168 (Tazarotene)

12. The method of claim 2, wherein the second RAR active agent is a RARγ selective agonist selected from CD437, CD2325, CD666, LY2813631, AGN 204647, and BMS961.

13. The method of claim 1, wherein the method comprises additionally administering at least one cancer chemotherapy agent.

14. The method of claim 1, wherein the RARγ selective agonist is AGN 204647.

15. The method of claim 1, wherein the wherein the immune checkpoint inhibitor comprises an antibody specific for PD-1.

16. The method of claim 1, wherein the wherein the immune checkpoint inhibitor comprises an antibody specific for PD-L1.

17. The method of claim 1, wherein the wherein the immune checkpoint inhibitor comprises an antibody specific for CTLA-4.

18. The method of claim 1, wherein the wherein the immune checkpoint inhibitor comprises an antibody specific for ICOS.

19. The method of claim 1, wherein the wherein the immune checkpoint inhibitor comprises an antibody specific for OX40.

20. The method of claim 1, wherein the wherein the immune checkpoint inhibitor comprises an antibody specific for TIM-3.

21. The method of claim 1, wherein the wherein the immune checkpoint inhibitor comprises an antibody specific for LAG-3.

22. The method of claim 1, wherein the wherein the immune checkpoint inhibitor comprises an antibody specific for B7-H3.

23. The method of claim 1, wherein the wherein the immune checkpoint inhibitor comprises an antibody specific for B7-H4.

24. The method of claim 1, wherein the wherein the immune checkpoint inhibitor comprises an antibody specific for BTLA.

* * * * *